(12) United States Patent
Papac et al.

(10) Patent No.: US 8,333,482 B2
(45) Date of Patent: Dec. 18, 2012

(54) OPHTHALMIC ENDOILLUMINATION WITH LIGHT COLLECTOR FOR WHITE PHOSPHOR

(75) Inventors: Michael James Papac, Tustin, CA (US); Christopher Horvath, Irvine, CA (US); Michael J. Yadlowsky, Irvine, CA (US); Ronald T. Smith, Irvine, CA (US)

(73) Assignee: Alcon Research, Ltd., Fort Worth, TX (US)

( * ) Notice: Subject to any disclaimer, the term of this patent is extended or adjusted under 35 U.S.C. 154(b) by 302 days.

(21) Appl. No.: 12/852,829

(22) Filed: Aug. 9, 2010

(65) Prior Publication Data
US 2011/0038174 A1    Feb. 17, 2011

Related U.S. Application Data

(60) Provisional application No. 61/233,383, filed on Aug. 12, 2009.

(51) Int. Cl.
*F21V 9/16* (2006.01)
(52) U.S. Cl. ............ 362/84; 362/293; 362/231
(58) Field of Classification Search ............ 362/84, 362/230, 231, 293, 572–574
See application file for complete search history.

(56) References Cited

U.S. PATENT DOCUMENTS

| | | | |
|---|---|---|---|
| 5,738,676 A * | 4/1998 | Hammer et al. | 606/4 |
| 6,841,804 B1 * | 1/2005 | Chen et al. | 257/98 |
| 7,144,131 B2 * | 12/2006 | Rains | 362/231 |
| 2006/0034084 A1 * | 2/2006 | Matsuura et al. | 362/293 |
| 2007/0081336 A1 * | 4/2007 | Bierhuizen et al. | 362/293 |
| 2007/0274068 A1 | 11/2007 | Berben et al. | |
| 2007/0297171 A1 | 12/2007 | Berben et al. | |
| 2008/0080206 A1 * | 4/2008 | Charles | 362/572 |
| 2008/0094835 A1 * | 4/2008 | Marra et al. | 362/247 |
| 2009/0052189 A1 | 2/2009 | Kon | |
| 2009/0054957 A1 | 2/2009 | Shanbaky | |
| 2009/0059359 A1 | 3/2009 | Nahm et al. | |

OTHER PUBLICATIONS

International Search Report for PCT/US2010/044,914, 4 pages.
Written Opinion of the International Searching Authority, International Application No. PCT/US2010/044,914, Nov. 3, 2010, 3 pages.

* cited by examiner

*Primary Examiner* — Julie Shallenberger
(74) *Attorney, Agent, or Firm* — Keiko Ichiye

(57) ABSTRACT

In one embodiment, an illuminator configured to emit light into an optical fiber includes at least one pump light source configured to emit short-wavelength light. The illuminator further includes a white phosphor disposed to receive the short-wavelength light and to emit white light in response. The illuminator also includes a light collector configured to collect the short-wavelength light at the white phosphor such that a brightness of the white light is greater than a brightness of the short-wavelength light.

9 Claims, 4 Drawing Sheets

Condensing Lens Design

Compound Parametric Condenser Design

TIR Collector Design

OPHTHALMIC ENDOILLUMINATION WITH LIGHT COLLECTOR FOR WHITE PHOSPHOR

RELATED APPLICATIONS

This application claims priority to U.S. provisional application Ser. No. 61/233,383, filed on Aug. 12, 2009, the contents which are incorporated herein by reference.

TECHNICAL FIELD OF THE INVENTION

The present invention relates to an illuminator for use in ophthalmic surgery and more particularly to an ophthalmic endoilluminator to produce a light suitable for illuminating the inside of an eye.

BACKGROUND OF THE INVENTION

Anatomically, the eye is divided into two distinct parts—the anterior segment and the posterior segment. The anterior segment includes the lens and extends from the outermost layer of the cornea (the corneal endothelium) to the posterior of the lens capsule. The posterior segment includes the portion of the eye behind the lens capsule. The posterior segment extends from the anterior hyaloid face to the retina, with which the posterior hyaloid face of the vitreous body is in direct contact. The posterior segment is much larger than the anterior segment.

The posterior segment includes the vitreous body—a clear, colorless, gel-like substance. It makes up approximately two-thirds of the eye's volume, giving it form and shape before birth. It is composed of 1% collagen and sodium hyaluronate and 99% water. The anterior boundary of the vitreous body is the anterior hyaloid face, which touches the posterior capsule of the lens, while the posterior hyaloid face forms its posterior boundary, and is in contact with the retina. The vitreous body is not free-flowing like the aqueous humor and has normal anatomic attachment sites. One of these sites is the vitreous base, which is a 3-4 mm wide band that overlies the ora serrata. The optic nerve head, macula lutea, and vascular arcade are also sites of attachment. The vitreous body's major functions are to hold the retina in place, maintain the integrity and shape of the globe, absorb shock due to movement, and to give support for the lens posteriorly. In contrast to aqueous humor, the vitreous body is not continuously replaced. The vitreous body becomes more fluid with age in a process known as syneresis. Syneresis results in shrinkage of the vitreous body, which can exert pressure or traction on its normal attachment sites. If enough traction is applied, the vitreous body may pull itself from its retinal attachment and create a retinal tear or hole.

Various surgical procedures, called vitreo-retinal procedures, are commonly performed in the posterior segment of the eye. Vitreo-retinal procedures are appropriate to treat many serious conditions of the posterior segment. Vitreo-retinal procedures treat conditions such as age-related macular degeneration (AMD), diabetic retinopathy and diabetic vitreous hemorrhage, macular hole, retinal detachment, epiretinal membrane, CMV retinitis, and many other ophthalmic conditions.

A surgeon performs vitreo-retinal procedures with a microscope and special lenses designed to provide a clear image of the posterior segment. Several tiny incisions just a millimeter or so in length are made on the sclera at the pars plana. The surgeon inserts microsurgical instruments through the incisions such as a fiber optic light source to illuminate inside the eye, an infusion line to maintain the eye's shape during surgery, and instruments to cut and remove the vitreous body.

During such surgical procedures, proper illumination of the inside of the eye is important. Typically, a thin optical fiber is inserted into the eye to provide the illumination. A light source, such as a metal halide lamp, a halogen lamp, a xenon lamp, or a mercury vapor lamp, is often used to produce the light carried by the optical fiber into the eye. The light passes through several optical elements (typically lenses, mirrors, and attenuators) and is emitted to the optical fiber that carries the light into the eye. The quality of this light is dependent on several factors including the types of optical elements selected.

SUMMARY OF THE INVENTION

In one embodiment of the present invention, an illuminator configured to emit light into an optical fiber includes at least one pump light source configured to emit short-wavelength light. The illuminator further includes a white phosphor disposed to receive the short-wavelength light and to emit white light in response. The illuminator also includes a light collector configured to collect the short-wavelength light at the white phosphor such that a brightness of the white light is greater than a brightness of the short-wavelength light.

In another embodiment of the present invention, and illuminator configured to emit light into an optical fiber includes a white phosphor, a plurality of pump lights sources, and a plurality of lenses. The plurality of pump light sources is spatially arranged around the white phosphor to direct short-wavelength light at the white phosphor from a plurality of respective directions. The plurality of respective directions subtends an angle greater than 180 degrees. Each one of the plurality of lenses is coupled to a respective one of the pump light sources to focus the short-wavelength light from the respective pump light source on the white phosphor

BRIEF DESCRIPTION OF THE DRAWINGS

For a more complete understanding of the present invention and the advantages thereof, reference is now made to the following description taken in conjunction with the accompanying drawings in which like reference numerals indicate like features and wherein.

DESCRIPTION OF THE INVENTION

Preferred embodiments of the present invention are illustrated in the Figures, like numerals being used to refer to like and corresponding parts of the various drawings.

Figure 1:
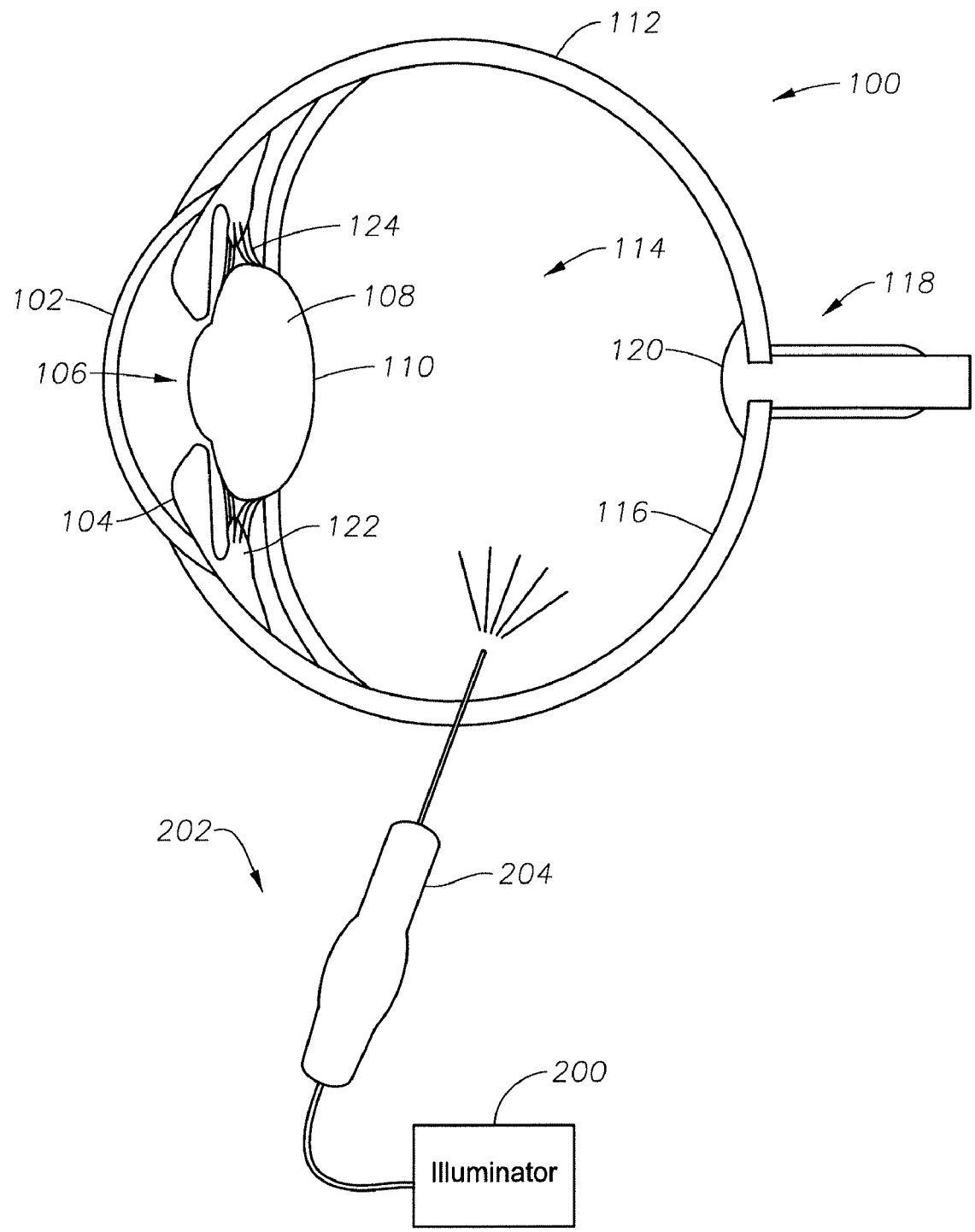
FIG. 1 illustrates the anatomy of the eye in which an ophthalmic endoilluminator in accordance with embodiments of the present invention may be placed.

FIG. 1 illustrates the anatomy of the eye into which the improved design for ocular implant provided by the present invention may be placed. Eye 100 includes cornea 102, iris 104, pupil 106, lens 108, lens capsule 110, zonules, ciliary body 120, sclera 112, vitreous gel 114, retina 116, macula, and optic nerve 120. Cornea 102 is a clear, dome-shaped structure on the surface of the eye acts as a window, letting light into the eye. Iris 104 is the colored part of the eye, called the iris, is a muscle surrounding the pupil that relaxes and contracts to control the amount of light entering the eye. Pupil 106 is the round, central opening of the iris. Lens 108 is the structure inside the eye that helps to focus light on the retina. Lens capsule 110 is an elastic bag that envelops the lens, helping to control lens shape when the eye focuses on objects at different distances. Zonules are slender ligaments that attach the lens capsule to the inside of the eye, holding the lens in place. The ciliary body is the muscular area attached to the lens that contracts and relaxes to control the size of the lens for focusing. Sclera 112 is the tough, outermost layer of the eye that maintains the shape of the eye. Vitreous gel 114 is the large, gel-filled section that is located towards the back of the eyeball, and which helps to maintain the curvature of the eye. Retina 116 is a light-sensitive nerve layer in the back of the eye that receives light and converts it into signals to send to the brain. The macula is the area in the back of the eye that contains receptors for seeing fine detail. Optic nerve 118 connects and transmits signals from the eye to the brain.

Ciliary body 122 lies just behind the iris 104. Attached to the ciliary body 122 are tiny fiber "guide wires" called zonules 124. Lens 108 is suspended inside the eye by the zonular fibers 124. Nourishment for the ciliary body 122 comes from blood vessels which also supply the iris 104. One function of ciliary body 122 is to control accommodation by changing the shape of the lens 108. When the ciliary body 122 contracts, the zonules 124 relax. This allows the lens 108 to thicken, increasing the eye's ability to focus up close. When looking at a distant object, ciliary body 122 relaxes, causing the zonules 124 to contract. The lens 108 then becomes thinner, adjusting the eye's focus for distance vision.

FIG. 1 also shows a cross sectional view of an ophthalmic endoilluminator 200, which may be an endoilluminator according to various embodiments of the present invention, located in an eye. FIG. 1 depicts the illuminator 200 coupled by an optical fiber to a handpiece 202 with probe 204 in use. Probe 204 is inserted into eye 100 through an incision in the pars plana region. Probe 204 illuminates the inside or vitreous region 114 of eye 100. In this configuration, probe 204 can be used to illuminate the inside or vitreous region 114 during vitreo-retinal surgery.

Ophthalmic endoilluminators have been previously based either on halogen tungsten lamps or high pressure arc lamps (metal-halides, Xe). The advantages of arc lamps are small emitting area (<1 mm), color temperature close to daylight, and longer life than in halogen lamps—400 hours vs. 50 hours. The disadvantage of arc lamps is high cost, decline in power, complexity of the systems and the need to exchange lamps several times over the life of the system.

LED based illuminators may provide considerably lower cost and complexity, and characteristic life times of 50,000 to 100,000 hours that would allow operating ophthalmic fiber illuminator for entire life of the instrument with very little drop in output and without a need of exchanging LEDs. A typical white LED may include a short-wavelength (ultra violet (UV)/violet/blue) LED exciting a white phosphor cap that emits white light, the source of light exciting the white phosphor layer being referred to as a "pump light source." One limit to the output brightness of the white LED is the total number of photons incident on the white phosphor. The short-wavelength LED may be placed near to, or in contact with, the white phosphor, but even in that case, a substantial amount of light may be emitted by the short-wavelength LED that is not incident on the white phosphor.

Unlike conventional illuminators, various embodiments of the present invention use a configuration of the white phosphor that allows large amounts of light to be collected from one or more short-wavelength LEDs or other pump light sources, allowing the amount of light incident on the white phosphor to be increased. This can increase the overall brightness of the light emitted by the white phosphor relative to the brightness of the short-wavelength LED. Specifically, a light collector directs more photons into the specific area of the white phosphor than would have been emitted in that area by the short-wavelength LED, which allows the incident photon density (and thus the emitted brightness from the white phosphor, to increase For purposes of this specification, "white phosphor" refers not only to broad band white phosphor materials but also to wavelength converting materials that either combine with light from the pump light source or combine light of different colors from multiple materials to produce bright light in a relatively broad spectral region.

Figure 2:
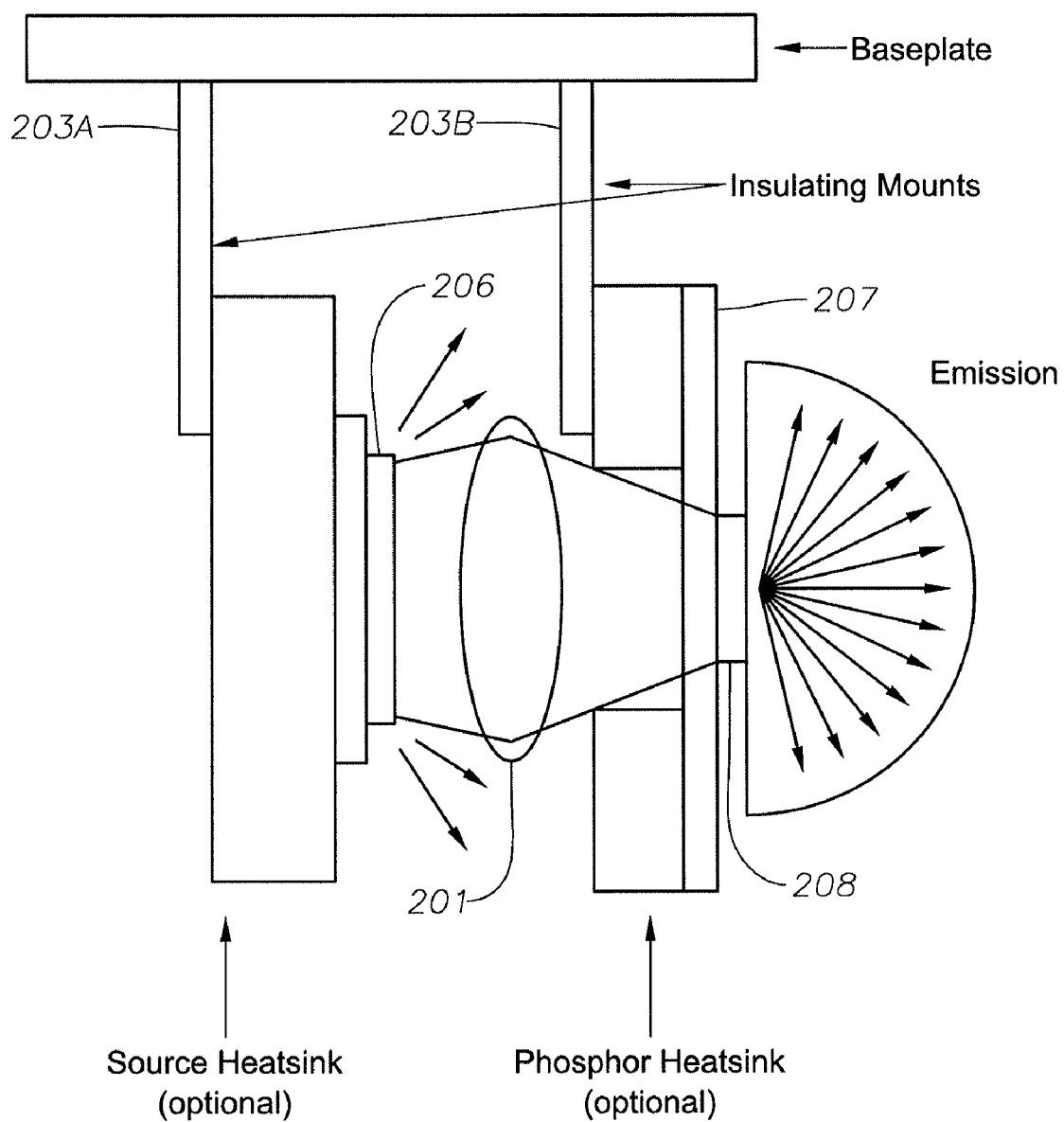
FIG. 2 illustrates in more detail an illuminator according to a particular embodiment of the present invention.

FIG. 2 illustrates a particular embodiment of the illuminator 200 in greater detail. In the depicted embodiment, a light collector 201 is disposed between two mounts 203A and 203B, the first mount 203A supporting a pump light source 206 producing short-wavelength light (shown as a large-area LED) and the second mount 203B having a transparent substrate 207 for a white phosphor 208 layered on the substrate 207. The light collector 201 collects light emitted over a wide angle and directs it onto a back surface of the substrate 207 so as to illuminate the white phosphor 208. This increases the photon density incident on the white phosphor 208 so as to produce a greater brightness emitted by the white phosphor 208.

Figure 3A:
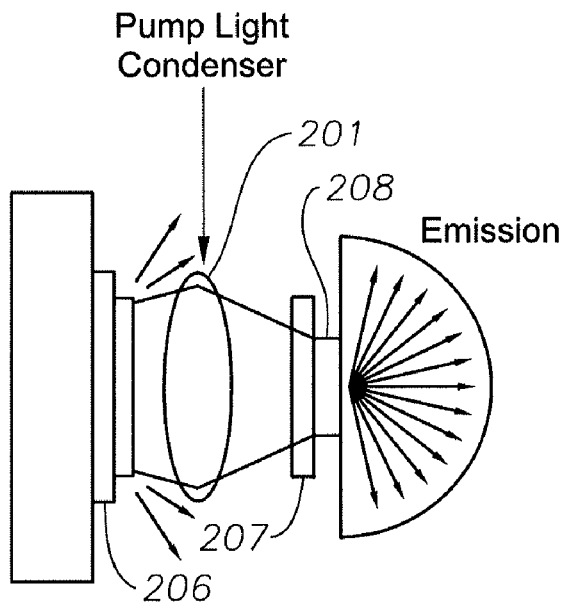
FIGS. 3A-3C illustrate several light collectors according to particular embodiments of the present invention.
Figure 3B:
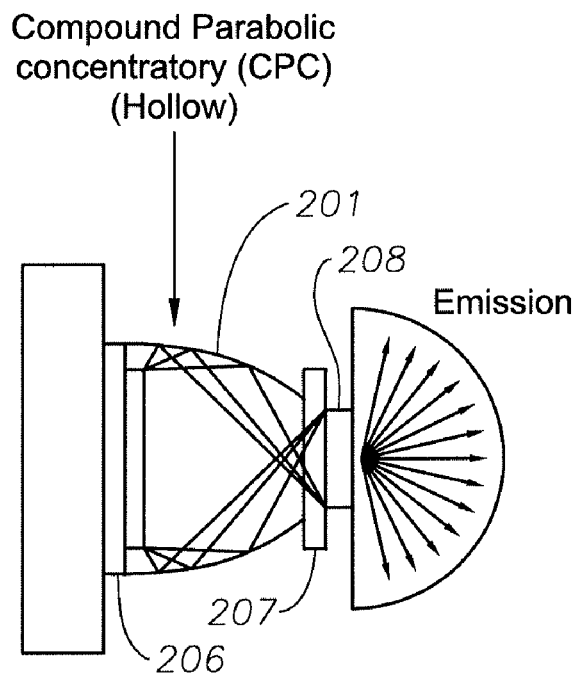
Figure 3C:
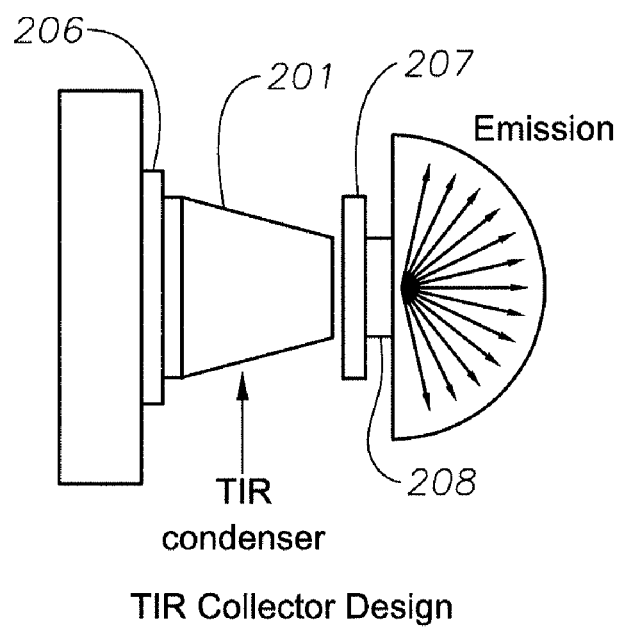

FIGS. 3A-3C illustrate various embodiments of light collector 201. In FIG. 3A, the light collector 201 is a condensing lens disposed having a diameter extending beyond the perimeter of the pump light source 206, thus allowing the lens to collect light emitted from the pump light source 206 over a wide angle. In FIG. 3B, the light collector 201 is a hollow compound parabolic concentrator that reflects light onto the white phosphor 208. In FIG. 3C, the light collector 201 is a refractive material configured with an angled surface and a suitable refractive index such that additional light is redirected to the white phosphor 208 by total internal reflection.

Figure 4:
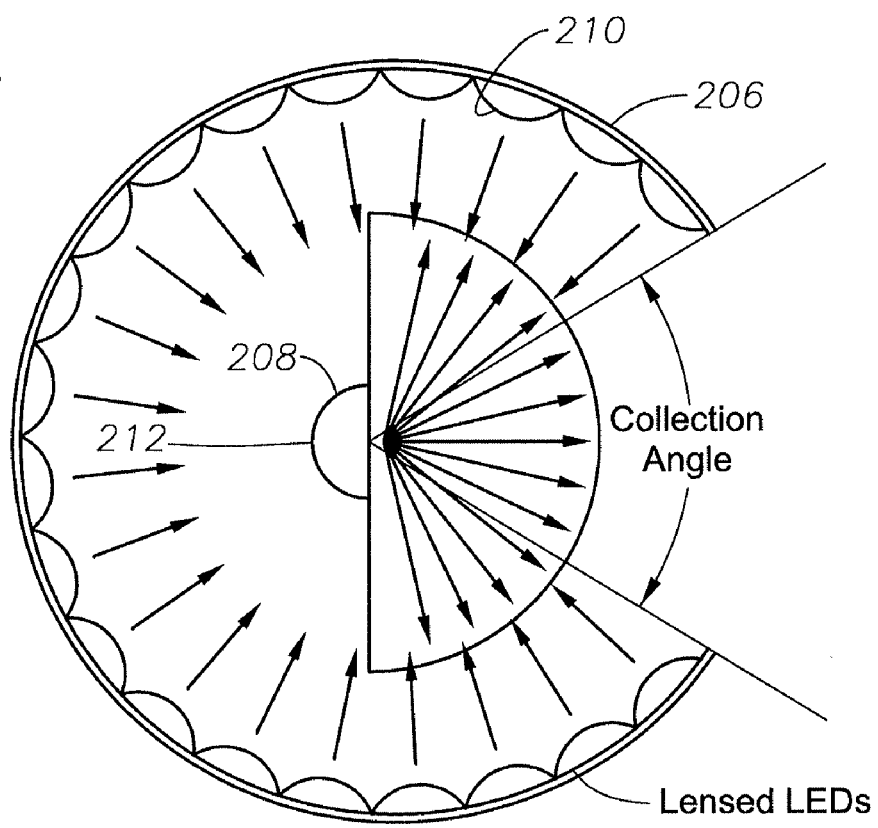
FIG. 4 illustrates a light collector arrangement with a plurality of pump light sources according to a particular embodiment of the present invention.

FIG. 4 illustrates an alternative embodiment of the illuminator 200 having multiple pump light sources 206 distributed around the white phosphor 208. The pump light sources 206 are arranged to subtend an angle around the white phosphor 208 that is greater than 180 degrees. A collection angle for light emitted from the white phosphor 208 is left open. The light collector 201 in the illustrated embodiment includes a plurality of lenses 210, each lens 210 focusing light from a respective pump light source 206 onto the white phosphor 208. The white phosphor 208 has a shaped back surface 212 in this instance so as to increase the direct incidence of light from the pump light sources 206, thereby increasing the overall photon density incident on the white phosphor 208.

The present invention is illustrated herein by example, and various modifications may be made by a person of ordinary skill in the art. Although the present invention is described in detail, it should be understood that various changes, substitutions and alterations can be made hereto without departing from the scope of the invention as claimed.

What is claimed is:

1. An illuminator configured to emit light into an optical fiber, comprising:
   a baseplate;

a first mount coupled to the baseplate and configured to support at least one pump light source configured to emit short-wavelength light;

a second mount coupled to the baseplate and comprising a substrate having a layer of white phosphor disposed to receive the short-wavelength light and to emit white light in response; and a light collector disposed between the first mount and the second mount configured to collect the short-wavelength light at the white phosphor such that a brightness of the white light is greater than a brightness of the short wavelength light, wherein the at least one pump light source comprises a plurality of pump light sources arranged to illuminate the white phosphor from a plurality of respective directions; and the light collector comprises a plurality of collecting lenses, each collecting lens connected to a respective one of the pump light sources.

2. The illuminator of claim 1, wherein the light collector is a condensing lens.

3. The illuminator of claim 1, wherein the light collector is a compound parabolic concentrator.

4. The illuminator of claim 1, wherein the light collector collects the short-wavelength light using total internal reflection.

5. The illuminator of claim 1, wherein the plurality of respective directions subtends an angle greater than 180 degrees.

6. The illuminator of claim 1, wherein the white phosphor is shaped to emit the white light in a narrower angle than an angle over which the white phosphor is illuminated by the short-wavelength light.

7. An illuminator configured to emit light into an optical fiber, comprising:

a white phosphor;

a plurality of pump light sources spatially arranged around the white phosphor and defining an opening with a collection angle, the collection angle formed from a first pump light source to the white phosphor to a second pump light source, the first and second pump light sources at opposite edges of the opening, the pump light sources configured to direct short-wavelength light at the white phosphor from a plurality of respective directions, the plurality of respective directions subtending a first angle greater than 180 degrees such that the collection angle is less than 180 degrees; and a plurality of lenses, each of the lenses coupled to a respective one of the pump light sources to focus the short-wavelength light from the respective pump light source onto the white phosphor, wherein the white phosphor comprises a shaped back surface formed to allow direct incidence of the short-wavelength light from the plurality of respective directions behind the white phosphor.

8. The illuminator of claim 7, wherein the pump light sources are substantially equal distance from the white phosphor.

9. The illuminator of claim 7, wherein the lenses are substantially equal distance from the white phosphor.

* * * * *